United States Patent [19]

Litchfield

[11] Patent Number: 4,533,017

[45] Date of Patent: Aug. 6, 1985

[54] SAFETY DEVICE AND HARNESS FOR USE IN SAME

[76] Inventor: Peter A. Litchfield, 335 A 37th St., SW., Calgary, Alberta, Canada, T3C 1R5

[21] Appl. No.: 576,723

[22] Filed: Feb. 3, 1984

[30] Foreign Application Priority Data

Sep. 27, 1983 [CA] Canada .................................. 437695

[51] Int. Cl.$^3$ .......................... A61F 5/04; A62B 37/00

[52] U.S. Cl. ....................................... 182/3; 128/87 R

[58] Field of Search ........................................ 182/3-8; 128/134, 103, 104, 87 R

[56] References Cited

U.S. PATENT DOCUMENTS

| | | | |
|---|---|---|---|
| 1,916,208 | 7/1933 | Diou . | |
| 1,927,469 | 9/1933 | Plumpton . | |
| 2,175,748 | 10/1939 | Dunn . | |
| 2,311,070 | 2/1943 | Morando . | |
| 2,946,396 | 7/1960 | McDougal . | |
| 2,979,153 | 4/1961 | Hoagland | 182/3 |
| 3,098,539 | 7/1963 | Gorman . | |
| 3,115,211 | 12/1963 | Ostrander, Jr. . | |
| 3,469,268 | 9/1969 | Phillips . | |
| 3,574,871 | 4/1971 | Greene . | |
| 3,701,395 | 10/1972 | Theobald . | |
| 3,775,782 | 12/1973 | Rice et al. . | |
| 3,933,154 | 1/1976 | Cabansag . | |
| 3,973,643 | 8/1976 | Hutchinson | 182/3 |
| 4,111,280 | 9/1978 | Devine et al. . | |
| 4,124,908 | 11/1978 | Burns et al. . | |
| 4,211,218 | 7/1980 | Kendrick | 128/134 |
| 4,252,214 | 2/1981 | Miller . | |

FOREIGN PATENT DOCUMENTS

| | | | |
|---|---|---|---|
| 298355 | 3/1930 | Canada . | |
| 790962 | 7/1968 | Canada . | |
| 1062401 | 9/1979 | Canada . | |
| 902429 | 8/1962 | United Kingdom | 182/3 |

*Primary Examiner*—Reinaldo P. Machado
*Attorney, Agent, or Firm*—Laubscher & Laubscher

[57] ABSTRACT

A safety device is disclosed comprising a harness made of flexible sheet, preferably of a strong canvas sheet provided with suitable fasteners and straps for securing the body of an injured person to the flexible base. In one embodiment, the base can be suspended on a pulley-and-rope mechanism secured to the top of an associated ladder. The invention is not limited to the combination including a ladder as the harness can be used with virtually any known suitable lifting device. The flexible harness can be guided along the associated ladder by a rigid U-shaped piece which is secured to the rear of the flexible base of the harness, the guide member being the only rigid portion of the entire harness. The harness and the rope-and-pulley system can be neatly tucked within an envelope near the top of the ladder whereby the contour of the ladder is generally unobstructed and the ladder can be used for purposes other than rescue at times at which there is no emergency, with the rescue harness being ready for a rescue application if necessary. The advance in the art is in the ease of folding the harness into a small space e.g. within a countour of a ladder, while retaining same in operative association with the respective ladder, also securing, by strategically located straps, safe securement of an injured person to the flexible canvas base.

13 Claims, 6 Drawing Figures

SAFETY DEVICE AND HARNESS FOR USE IN SAME

BACKGROUND OF THE INVENTION

The present invention relates, in general terms, to a rescue device and in particular a device for lifting or lowering a body of an injured person in case of emergency, such as a fire, cave-in or the like. The invention is not limited to such field of application but it is its primary objective to provide an emergency rescue device.

Prior art to which the present invention pertains is represented by issued U.S. Patents to which a brief reference will be made hereinafter. U.S. Pat. No. 1,916,208 issued July 4, 1933 to J. Diou, shows an extension ladder including two ladder sections slidably connected to each other and telescoping members slidable relative to each other and secured one to each of the two ladders. Means are provided for slidably relatively telescoping the members and held by the same. The means is adapted to be secured to the body of a person on the ladder. A similar safety grip for ladders is described in U.S. Pat. No. 1,927,469 issued Sept. 19, 1933 to E. F. Plumpton. U.S. Pat. No. 2,175,748 issued Oct. 10, 1939 to J. S. Dunn shows a rescue apparatus of the type of a rigid platform which can be moved along a wall of a building or the like and to which a person being rescued is secured by straps. U.S. Pat. No. 2,311,070 issued Feb. 16, 1943 to E. R. Morando shows a cage-like device slidably mounted on a ladder, the ladder being also provided with a suitable winch for moving the cage of the life-saving device along the ladder thus being capable of lifting or lowering a body in the cage. U.S. Pat. No. 3,098,539 shows an aerial harness made of flexible belts or straps and adapted to be secured to a human body. U.S. Pat. No. 3,115,211 issued Dec. 24, 1963 to J. A. Ostrander, Jr. describes a platform which is movable along an associated ladder. U.S. Pat. No. 3,701,395 issued Oct. 31, 1972 to S. J. Theobald shows another embodiment of harness having straps interconnected by a central base section. U.S. Pat. No. 4,252,214 issued Feb. 24, 1981 to J. W. Miller shows a safety descent device whereby a person climbing a ladder is connected with a harness suspended from an overhead pulley, the pulley itself not being associated with the ladder arrangement. Finally, U.S. Pat. No. 4,111,280 issued Sept. 5, 1978 to D. R. Devine et al shows a fall prevention safety climbing device for workmen ascending and descending ladders on tall structures, having a sleeve including a locking pawl adapted for attachment to a workman's safety belt.

In summary, the above prior art shows that it is recognized as a practical solution (a) to use a suitable harness or a safety belt for securement of a human body to a suspending device and (b) to use the device in combination with a ladder thus utilizing the ladder in a more versatile fashion.

From the standpoint of the present invention, the drawback of prior art as represented by the above patents is seen in cumbersome arrangement of the components of the known rescue devices which results in that the ladder can seldom be used for a purpose other than for the rescue operations. Relatively expensive and space consuming arrangement of rigid cages, boards or the like is also seen as a disadvantage not only from the standpoint of utilization of the ladder structure itself for ordinary, non-rescue operations, but also from the standpoint of storage.

SUMMARY OF THE INVENTION

Accordingly, it is an object of the present invention to provide a rescue device which would be capable to utilize as its basic supporting structure an ordinary ladder and which would neatly fold such that, even while connected to the ladder in the folded state, it does not hamper the use of the associated ladder for ordinary, non-rescue purposes such as painting, repairs, etc.

In general terms, the present invention can be defined in one aspect thereof as providing, for use in a rescue device for lifting or lowering an injured person or the like, a harness, comprising, in combination: a body backing base section made of a foldable, flexible sheet material and including a normally upper end section provided with a fastening device for securing the base section to a rope or the like, said base section including a head portion disposed at a close spacing from said fastening device, a central portion spaced from the head section a distance corresponding to the distance between the head and the level of the part of the human chest disposed slightly below the level of armpits of an average grown-up human body, and a lower portion disposed normally below the central portion; said head portion being provided with first strap means secured to the head portion and adapted to hold the head of an injured person in contact with the head portion; said central portion being provided with transverse, second strap means adapted to wrap around the chest of an injured person to hold the body of the injured person secured to the base section; said lower portion being provided with third strap means adapted to be secured to the human body or the like at the lower torso thereof to support the human body on said base section as the base is suspended on said fastening device.

In another aspect, the invention can be generally defined as providing a rescue device comprising the harness as described above in combination with a ladder having a normally upper end provided with a head frame member fixedly secured to side pieces of the ladder and equipped with a lifting pulley-and-rope mechanism including a pulley structure connected to the head frame member, one end of the rope of the pulley-and-rope mechanism being secured to a harness, and also the harness being also combined with flexible wrapper means disposed near said head frame member and adapted to envelope the harness and the maintain same in a folded state at the normally upper end of the ladder.

BRIEF DESCRIPTION OF THE DRAWINGS

The invention will now be described by way of a preferred embodiment with reference to the accompanying drawings. In the drawings.

DETAILED DESCRIPTION OF PREFERRED EMBODIMENT

Figure 5:
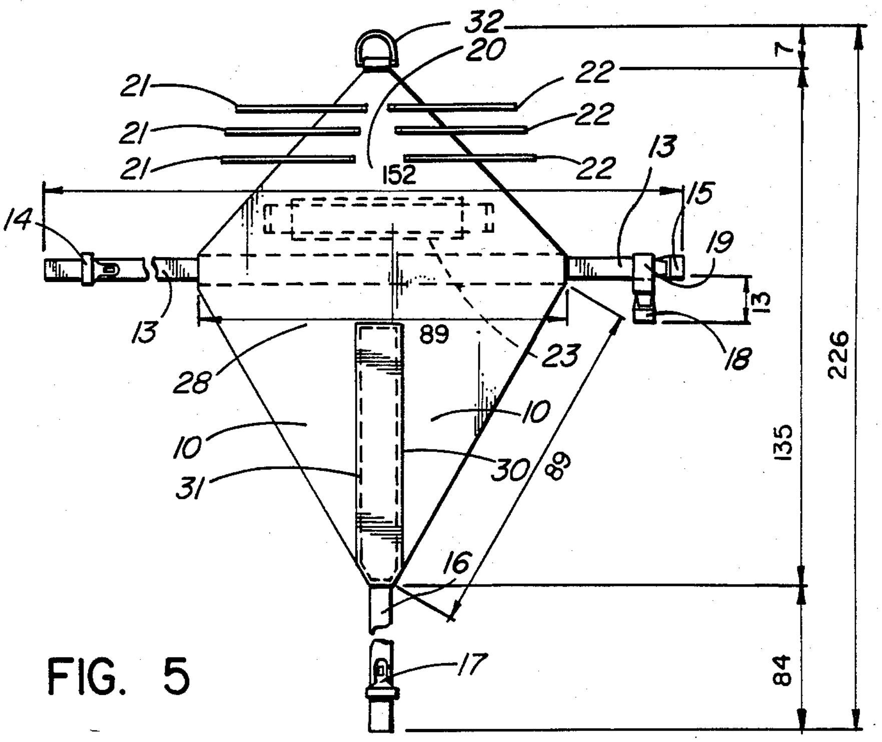
FIG. 5 is a top plan view of flattened-out harness of the present invention with certain dimensions being shown in centimeters as an indication of the preferred size of the harness used for an average grown-up human body.
Figure 6:
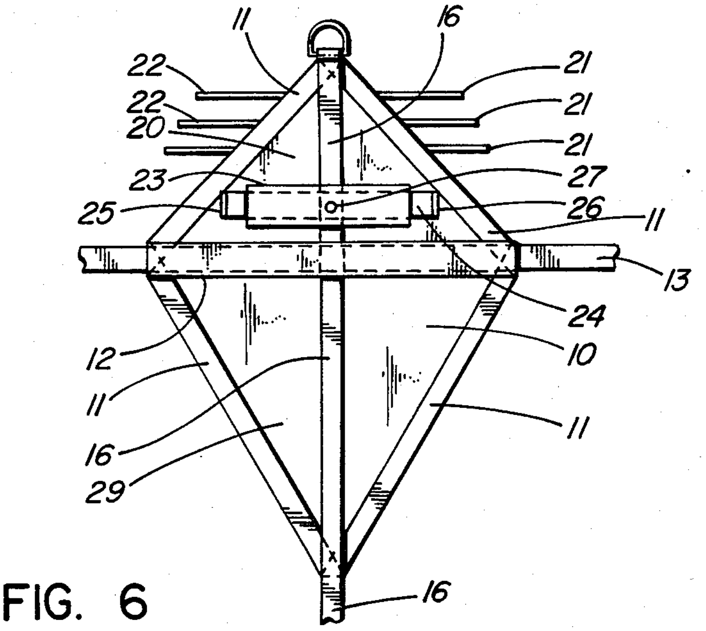
FIG. 6 is a bottom plan view of the arrangement shown in FIG. 5.

Turning firstly to the representations in FIGS. 5 and 6, the harness according to the present invention is basically formed by a body-backing base section 10 which is made of a heavy canvas which is strong but flexible to allow the folding of the entire base section. In a flattened-out state, the base section has a diamond-shaped contour as seen in FIGS. 5 and 6.

Along the periphery of the base section, a nylon webbing 11 is stitched to the base, to reinforce same. At the rear surface of the base (visible in FIG. 6), a transverse sleeve 12 receives a strap 13 whose one end is provided with a plug 14 of a buckle, the other end being provided with a socket 15 of the buckle. The strap 13 is also provided with the usual length adjustment means which is not shown in the drawings as it forms a well known feature of safety belts or the like. Fixedly secured by a stitching to the canvas forming the base section 10 is a longitudinal strap 16 which extends from the top of FIG. 6 beyond the lowermost end of the base 10, as best seen in FIG. 16. The free end of the strap 16 is provided with a plug 17 of another buckle, the receiving socket of that buckle being socket 18 which is secured to a short strap 19 slidable along the above strap 13.

The upper section of the base 10 (designated roughly with reference numeral 20), is also referred as the "head portion" of the base 10. It is provided with a series of straps 21, 22. The left-hand side series of straps 21 in FIG. 5 is provided with the hook-part of a "VELCRO" (Trademark) fastener, while the second group of straps 22 is provided with a complementary pile section of the same fastener. The straps 21, 22 are of a length sufficient to engage the head of the grown-up human such as to hold same firmly against the portion 20 of the base section 10.

Another sleeve 23 (FIG. 6) receives a "U"-shaped, rigid bar 24 which is of a flattened rectangular configuration in cross-section, best visible in FIG. 6 when viewing the two arms 25, 26 of the "U". The bar 24 is secured to the base 10 by a rivet 27.

The location at which the strap 13 is secured to the base 10 is also referred to as a central portion 28 (FIG. 5) and the portion 29 (FIG. 6) roughly designates what is generally referred to as the lower portion of the base section 10. The overall disposition of the head, central and lower portions 20, 28 and 29, when the rescue device is to be used for a grown-up person, is apparent from the dimensions shown in FIG. 5.

In a top plan view of FIG. 5, another pocket 30 is shown within which is received an upper elongated strip of a flat foam padding 31 which, while providing protection to the person rescued by the device, still allows convenient folding of the harness.

Figure 1:
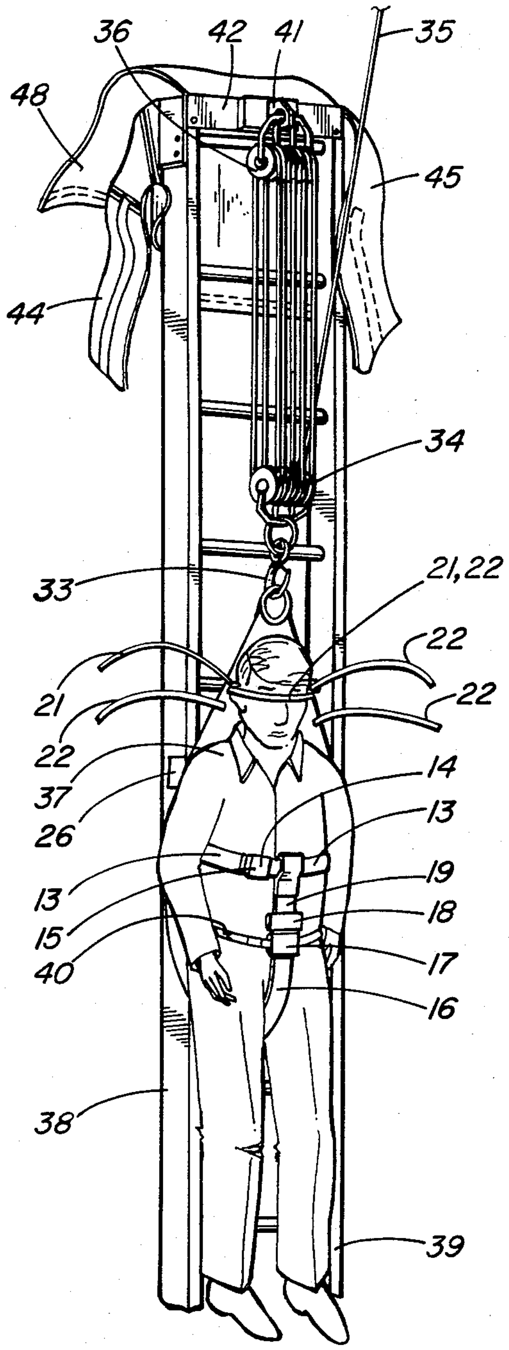
FIG. 1 is a simplified, perspective view showing the device of the present invention in use.

On the top of the head portion 20 is mounted an eyelet 32 for securing the harness to a hook 33 (FIG. 1) connected to a movable pulley set 34 operatively associated, by a rope 35 with an upper pulley set 36. Each of the pulley sets 34, 36 has three pulleys, whereby the force required at the free end of the rope 35 (the upper portion of FIG. 1) is substantially reduced and allows for convenient lifting or lowering of an injured person 37. It is shown in FIG. 1 that, in this embodiment, the arms 25, 26 (only 26 visible in FIG. 1) can slide along side pieces 38, 39 of an associated ladder. In the operative state shown in FIG. 1, only one pair of the straps 21, 22 (the central pair) is used in holding the head of the injured person firmly against the base section 10 at its head portion 20. The strap 13 is now wrapped around the chest of the injured person and held in such a position by the buckle of which only the socket 15 is visible in FIG. 1. The strap 19 and its socket 18 are shown as being connected, via the plug member 17, which the strap 16 thus firmly holding the injured person secured to the base section 10. If desired, an auxiliary strap 40 can be secured to the canvas base section 10 at the level of the applied plug member 17. The auxiliary strap 40 which can have its own buckle for convenient connecting and disconnecting is only indicated in FIG. 1.

Figure 4:
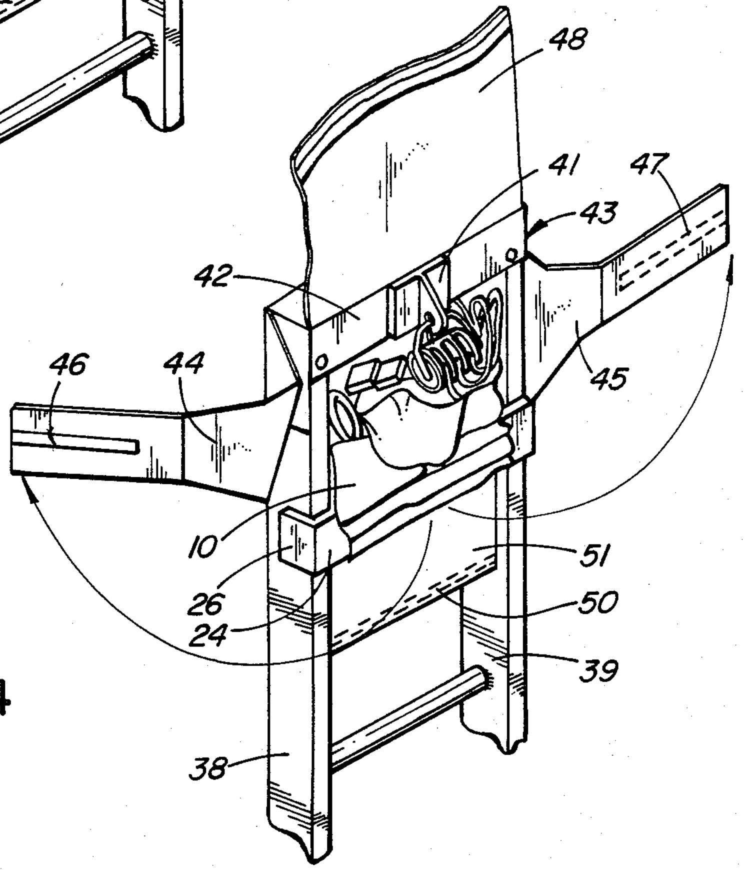
FIG. 4 is a view similar to that of FIG. 3 and showing the wrapper in a fully open or unwrapped state.

The upper pulley set 36 is secured to a securement member 41 having the shape of a bracket welded to one side 42 of a head frame 43 which is box-shaped and is so dimensioned as to become conveniently secured the side pieces 38, 39 of the associated ladder. The dimensioning of the pulley sets 36, 34 is preferably made such as to allow the tucking of the three pulley sets 34 into the head frame 43, as indicated in FIG. 4. In such a folded position, the base section 10 is folded and inserted into the space between the bar 24 and the head piece 43 and otherwise limited by the wide or depth of the side pieces 38, 39 corresponding to the width of the box of the head piece 43.

Figure 3:
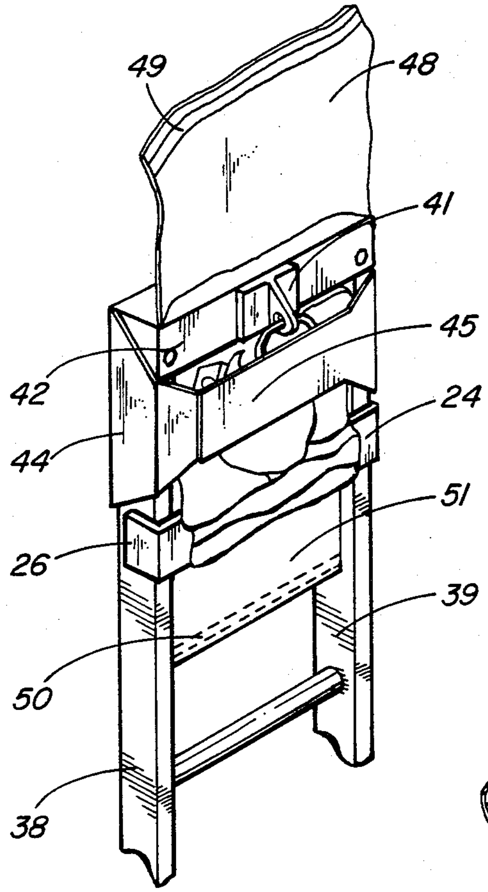
FIG. 3 is a view similar to that of FIG. 2 but showing the wrapper of the folded harness partly unwrapped.

The overall arrangement is maintained in such a position by a preferred embodiment of a wrapper made of flexible sheet material such as canvas, and having a flat, rectangular rear section which is not visible in the drawings but which corresponds in width to the width of the ladder, i.e. to the distance of the outer surfaces between the side pieces 38, 39. The panel is integral with a first flap 44 and with a second flap 45 which can wrap around the ladder as best seen in FIG. 3, to be maintained in such a position by the respective parts 46, 47 of a VELCRO (Trademark) fastener, secured to the flaps 44, 45 in a longitudinal direction.

Figure 2:
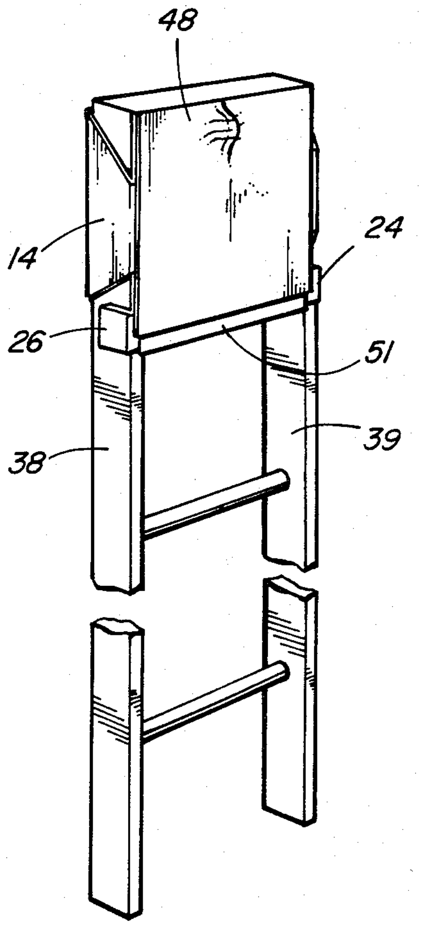
FIG. 2 is a simplified, perspective view of a ladder equipped with the device of the present invention and showing the device in a fully folded state.

An upper flap 48, also integral with the panel, extends over the top of the head frame 43 and is provided with a first strip 49 of a VELCRO (Trademark) fastener which is disposed transversely of the flap 48. A complementary strip 50 of the same fastener is disposed transversely of the end edge of a lower flap 51 integral with the first mentioned panel in the same fashion as the remaining flaps referred to above. It will be appreciated from the representation of FIGS. 3 and 4 that the pulley set, the base section 10 and the rope used in the device can all be neatly tucked into the space provided and that the lower flap 51 is so arranged as to neatly envelope the lowermost edge of the glide bar 24 to completely enclose the rescue assembly. The completely enclosed state is shown in FIG. 2. It will be seen that the present invention thus provides a rescue device which, while providing virtually all of the advantages of prior art as referred to above, does not suffer the drawback of cumbersome storage and operation and which does not hinder the regular operation of the ladder which can be continued with the rescue apparatus stored near the top of the ladder and ready for use at any time.

Those skilled in the art will appreciate that the harness of the present invention does not have to be used in association with a ladder. Many modifications may exist of the preferred embodiment described above, without departing the scope of the present invention as set forth in the accompanying claims.

I claim:

1. A rescue device of the type adapted to be applied to to the body of an injured person for lifting or lowering the injured person, said rescue device comprising, in combination:

(a) a body backing base section made of a foldable, flexible sheet material and including a normally upper end section provided with a fastening device for securing the base section to a rope or the like, said base section including a head portion disposed at a close spacing from said fastening device, a central portion spaced from said head portion a distance corresponding to the distance between the head and the level of the part of the human chest disposed slightly below the level of armpits of an average grown-up human body, and a lower portion disposed normally below said central portion;

(b) first strap means secured to said head portion for holding the head of an injured person in contact with said head portion;

(c) transverse second strap means connected with said central portion for wrapping around the chest of an injured person, thereby to hold the body of the injured person to the base section;

(d) a band (16) secured at one end to, and extending downwardly coextensively with the longitudinal certerline of, said base section lower portion; and (e) buckle means for releasably fastening the other end of said band with said second strap means, said buckle means including a first part (17) secured to said other end of said band, and a complementary second part (18) secured to said second strap means.

2. A rescue device for lifting or lowering an injured person, said rescue device comprising, in combination:

(a) a body backing base section made of a foldable, flexible sheet material and including a normally upper end section provided with a fastening device for securing the base section to a rope or the like, said base section including a head portion disposed at a close spacing from said fastening device, a central portion spaced from said head portion a distance corresponding to the distance between the head and the level of the part of the human chest disposed slightly below the level of armpits of an average grown-up human body, and a lower portion disposed normally below said central portion;

(b) first strap means secured to said head portion for holding the head of an injured person in contact with said head portion;

(c) transverse second strap means connected with said central portion for wrapping around the chest of an injured person to hold the body of the injured person to said base section;

(d) third strap means connected with said lower portion for fastening to the human body or the like at the lower torso thereof, thereby to support the human body on said base section as the base is suspended on said fastening device; and (e) guide bar attachment means for securing to said base section a rigid guide bar for guiding the bar along a ladder as the suspended base moves along the ladder.

3. The device as claimed in claim 2, wherein said guide bar securement means is a sleeve disposed transversely of the base section at a level between the head portion and the central portion and disposed at a rear surface of the base section, said rear surface being turned away from the injured body or the like when the harness is in use.

4. The device as claimed in claim 3, in combination with a U-shaped guide bar of a rectangular cross-section, the arms of the "U" extending away from said rear surface and being spaced apart a distance allowing the sliding engagement between side pieces of an associated ladder and the inside surfaces of said arms.

5. The device as claimed in claim 2, further comprising a flexible foam padding disposed generally centrally of the base section at said lower portion thereof.

6. The device as claimed in claim 5, wherein said padding extends at least partly into the central portion of the base section.

7. The device as claimed in claim 2, in combination with a head frame member having a rectangular box-shaped configuration whose length corresponds to the width of an associated ladder as measured at side pieces of the ladder, said head frame member including securement means for securing to the head frame member a lifting mechanism such as pulley of a pulley-and-rope mechanism.

8. The device as claimed in claim 7, wherein the width of the head frame member is sufficient to allow the tucking of the lifting mechanism into the head frame member when the latter is fixedly secured to a respective ladder at one end thereof.

9. A rescue device comprising, in combination:

(A) a ladder having a normally upper end provided with a head frame member fixedly secured to side pieces of the ladder and equipped with a lifting pulley-and-rope mechanism including a pulley structure connected to the head frame member, one end of the pulley-and-rope mechanism being secured to a harness;

(B) said harness comprising, in combination:

(a) a body backing base section made of a foldable, flexible sheet material having a diamond-shaped contour and including a normally upper end section provided with a fastening device by which it is secured to said mechanism, said base section including a head portion disposed at a close spacing from said fastening device, a central portion spaced from the head section a distance corresponding to the distance between the head and the level of the part of the chest disposed slightly below the level of armpits of an average grown-up human body, and a lower portion disposed normally below the central portion;

(b) said head portion being provided with first strap means secured to the head portion and adapted to hold the head of an injured person in contact with the head portion;

(c) said central portion being provided with transverse, second strap means adapted to wrap around the chest of an injured person to hold the torso of the injured person secured to the base section;

(d) said lower portion being provided with third strap means adapted to be secured to the injured human body or the like at the lower torso to support the human body on said base section as the base is suspended on said pulley-and-rope mechanism;

(e) a glide bar secured to the base and being of the type of a rigid guide bar for guiding the base along the ladder as the suspended base moves along the same; and (C) a flexible wrapper means disposed near said head frame member and adapted to envelope the harness and the maintain same in a folded state at the normally upper end of the ladder.

10. A resue device as claimed in claim 9, wherein said glide bar is a U-shaped glide bar of a rectangular cross-section, the arms of the "U" extending away from a rear surface of the base and being disposed each at a close but sliding relationship from an exterior surface of a respective side piece of the ladder, whereby the glide member is slidable along the side pieces of said ladder.

11. A rescue device as claimed in claim 10, wherein the second strap means is a strap mounted in a sleeve of the base section and freely displaceable longitudinally of said sleeve, the ends of the strap being provided with respective members of a buckle for convenient securement of the ends of the strap to each other, said strap being generally coincident with the minor main axis of the diamond shape of the base.

12. A rescue device as claimed in claim 11, wherein said third strap means is a band whose first end is fixedly secured to the base section at the rear surface thereof and near said fastening device, then extends in coincidence with a major, longitudinal axis of the diamond shape of the base section, the free end of the band forming an extension of said main axis and being provided with fastener means for securing same to said second strap means.

13. A rescue device as claimed in claim 12, wherein said wrapper means includes guide bar holding means arranged to hold the guide bar near the top end and in engagement with said side pieces when the harness and the pulley-and-rope mechanism is in a folded state.

* * * * *